United States Patent [19]

Schacht et al.

[11] 4,060,609
[45] Nov. 29, 1977

[54] BIPHENYLYL ETHERS AND METHOD OF USE

[75] Inventors: Erich Schacht; Werner Mehrhof; Rochus Jonas; Herbert Nowak; Zdenek Simane, all of Darmstadt, Germany

[73] Assignee: Merck Patent Gesellschaft mit beschrankter Haftung, Darmstadt, Germany

[21] Appl. No.: 518,811

[22] Filed: Oct. 29, 1974

[30] Foreign Application Priority Data

Oct. 31, 1973    Germany ............................... 2354444

[51] Int. Cl.$^2$ .................. C07D 295/08; A61K 31/535
[52] U.S. Cl. ............................... 424/244; 424/248.56; 424/248.58; 424/267; 424/274; 424/330; 544/129; 544/167; 544/174; 260/239 B; 260/247.5 G; 260/247.7 S; 260/293.64; 260/293.69; 260/293.71; 260/293.78; 260/293.83; 260/326.5 M; 260/570.7
[58] Field of Search ................. 260/239 B, 326.5 FM, 260/293.83, 247.7 S, 293.64, 293.69, 293.71, 293.78, 247.5 G, 293.83, 326.5 M; 424/244, 248.56, 248.58, 267, 274

[56] References Cited

U.S. PATENT DOCUMENTS

| 3,337,628 | 8/1967 | Crowther et al. ................ 260/570.7 |
| 3,501,769 | 3/1970 | Crowther et al. ............. 260/501.17 |

FOREIGN PATENT DOCUMENTS

| 1,494,749 | 8/1967 | France ............................. 260/570.7 |
| A92,612 | 10/1968 | France ............................. 260/570.7 |

OTHER PUBLICATIONS

Crowther et al. III, J. Med. Chem., vol. 11, pp. 1009–1013 (1968).
Kurihara et al., Chem. Abst., vol. 64, col. 12664 (1966).
Ing et al., J. Pharm. Pharmacol., vol. 4, pp. 21 to 26 (1952).

Primary Examiner—Henry R. Jiles
Assistant Examiner—R. W. Ramsuer
Attorney, Agent, or Firm—Millen & White

[57] ABSTRACT

Biphenylyl ethers of the formula R—O—CH$_2$—CR$_1$(OH)—CH$_2$Z wherein R$_1$ is H or CH$_3$; Z is dialkylamino of 2-8 carbon atoms, morpholino, pyrrolidino, piperidino, homopiperidino, hydroxypyrrolidino, hydroxypiperidino or hydroxyhomopiperidino; R is either biphenylyl substituted by at least one of F, Cl, Br, I, CF$_3$, NO$_2$ and piperidino or, when R$_1$ is CH$_3$ or when Z is homopiperidino, hydroxypyrrolidino, hydroxypiperidino or hydroxyhomopiperidino, unsubstituted biphenyl, and the physiologically acceptable acid addition salts thereof, possess cholesterol blood-level-lowering activity and can be produced by reacting a compound of the formula R—O—CH$_2$—Y wherein Y is

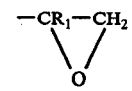

or —CR$_1$(OH)—CH$_2$X, X being Cl, Br, I or a free or functionally modified OH-group, with an amine of the formula H-Z.

21 Claims, No Drawings

BIPHENYLYL ETHERS AND METHOD OF USE

BACKGROUND OF THE INVENTION

This invention relates to novel biphenylyl ethers.
Similar compounds are described in Chemical Abstracts, vol. 46, 6616 (1952), and vol. 64, 12664 (1966).

SUMMARY OF THE INVENTION

In a composition aspect, this invention relates to novel biphenylyl ethers of the general Formula 1

, $R-O-CH_2-CR_1(OH)-CH_2Z$      1 wherein $R_1$ is H or $CH_3$, Z is dialkylamino of 2–8 carbon atoms, morpholino or pyrrolidino, piperidino or homopiperidino optionally substituted by a hydroxy group; and R is either biphenylyl substituted by at least one of F, Cl, Br, I, $CF_3$, $NO_2$ or piperidino or when either or both of $R_1$ is $CH_3$ and Z is homopiperidino, hydroxypyrrolidino, hydroxypiperidino or hydroxyhomopiperidino, unsubstituted biphenyl; and the physiologically acceptable acid addition salts thereof.

In another composition aspect, this invention relates to pharmaceutical compositions comprising a compound of this invention.

In process aspects, this invention relates to processes for the production of the novel compounds of this invention and to their use to lower cholesterol blood-level-lowering activity.

DETAILED DISCUSSION

The compounds of Formula I possess with good compatibility, valuable pharmacological properties, more particularly, cholesterol blood-level-lowering and triglyceride blood-level-lowering activities. These activities can be measured in rats in accordance with the methods developed by Levine and collaborators (Automation in Analytical Chemistry, Technicon Symposium, 1967, Mediad, New York, pp. 25–28) and by Noble and Campbell (Clin. Chem. 16 [1970], pp. 166–170). These products also exhibit very high thrombocyte aggregation inhibition activity and β-receptor-blocking activity, which can likewise be determined according to methods customary for this purpose. The compounds thus exhibit a very broad spectrum of pharmacological activity.

The novel compounds of this invention can be utilized as medicinal agents in the human and veterinary medicine, particularly for the treatment of hyperlipoproteinemias and for the prophylaxis and for the treatment of cardiovascular diseases. They can also be used as intermediates for the preparation of other medicines.

In the compounds of this invention, R is preferably monosubstituted biphenylyl, but can also be disubstituted, as well as tri-, tetra-, penta-, hexa-, hepta-, octa-, or nona-substituted. As substituents, fluoro, chloro and nitro are preferred. Biphenylyl-4 groups substituted in the 4'-position are preferred, especially 4'-fluorobiphenylyl-4, 4'-chlorobiphenylyl-4 and 4'-nitrobiphenylyl-4, as well as 4'-bromobiphenylyl-4, 4'-iodobiphenylyl-4, 4'-trifluoromethylbiphenylyl-4, and 4'-piperidinobiphenylyl-4. Examples of others are biphenylyl-4 groups substituted in the 2'-position or 3'-position, e.g., 2'-fluorobiphenylyl-4, 2'-chlorobiphenylyl-4, 2'-bromobiphenylyl-4, 2'-iodobiphenylyl-4, 2'-trifluoromethylbiphenylyl-4, 2'-nitrobiphenylyl-4, 2'-piperidinobiphenylyl-4, 3'-fluorobiphenylyl-4, 3'-chlorobiphenylyl-4, 3'-bromobiphenylyl-4, 3'-iodobiphenylyl-4, 3'-trifluoromethylbiphenylyl-4, 3'-nitrobiphenylyl-4 and 3'-piperidinobiphenylyl-4.

Other examples of monosubstituted biphenylyl are 2- and 3-fluorobiphenylyl-4, 2- and 3-chlorobiphenylyl-4; 2- and 3-bromobiphenylyl-4; 2- and 3-iodobiphenylyl-4, 2- and 3-trifluoromethylbiphenylyl-4; 2- and 3-nitrobiphenylyl-4; 2- and 3-piperidinobiphenylyl-4; 3-, 4-, 5-, 6-, 2'-, 3'- and 4'-fluorobiphenylyl-2; 3-, 4-, especially 5-, 6-, 2'- 3'- and 4'-chlorobiphenylyl-2; 3-, 4-, 5-, 6-, 2'-, 3'- and 4'-nitrobiphenylyl-2; 2-, 4-, 5-, 6-, 2'-, 3'- and particularly 4'-fluorobiphenylyl-3; 2-, 4-, 5-, 6-, 2'-, 3'- and particularly 4'-chlorobiphenylyl-3; 2-, 4-, 5-, 6-, 2'-, 3'- and 4'- nitrobiphenylyl-3.

Of the disubstituted biphenylyl groups, those substituted by two identical or different halogen atoms, especially dihalobiphenylyl-4 groups are preferred, especially the difluoro-, fluorochloro-, dichloro-, fluorobromo- and chlorobromobiphenylyl groups, e.g., 2',4'-difluorobiphenylyl-4, 3'-chloro-4'-fluorobiphenylyl-4, 2',4'-dichlorobiphenylyl-4, 2-bromo-4'-fluorobiphenylyl-4 and 2-bromo-4'-chlorobiphenylyl-4.

$R_1$ is preferably hydrogen.

Z preferably is piperidino or pyrrolidino but can also be homopiperidino or morpholino. Of the pyrrolidino, piperidino and homopiperidino groups substituted by a hydroxy groups, those wherein the hydroxy group is beta to the amino nitrogen atom and especially 3-hydroxypiperidino are preferred. When Z is dialkylamino, the alkyl groups are preferably identical. Examples of such alkyl groups are methyl, ethyl, n-propyl, isopropyl, n-butyl and isobutyl. The corresponding preferred dialkylamino groups are dimethylamino, diethylamino, di-n-propylamino, diisopropylamino, di-n-butylamino and diisobutylamino. Of the dialkylamino groups with different alkyl groups, methylethylamino is preferred.

Accordingly, preferred of the compounds of Formula 1 are those wherein at least one of R, $R_1$ and/or Z has one of the above preferred values.

Several of these preferred groups of compounds can be expressed by the partial Formulae 1a through 1n, which correspond to Formula 1, i.e., the groups not defined therein have the values given for Formula 1:

1a R is biphenylyl mono- or disubstituted by F, Cl, Br, I, $CF_3$ or $NO_2$;
1b R is biphenylyl monosubstituted by F, Cl, Br, I, $CF_3$ or $NO_2$;
1c R is biphenylyl-4 monosubstituted by F, Cl, Br, I, $CF_3$ or $NO_2$;
1d R is 4'-fluorobiphenylyl-4, 4'-chlorobiphenylyl-4 or 4'-nitrobiphenylyl-4;
1e $R_1$ is hydrogen, especially those of 1a, 1b, 1c and 1d;
1f Z is morpholino, piperidino, pyrrolidino or homopiperidino, especially those of 1a, 1b, 1c, 1d and 1e;
1g Z is morpholino or piperidino, especially those of 1a, 1b, 1c, 1d and 1e;
1h R is 4'-fluorobiphenylyl-4, 4'-chlorobiphenylyl-4, 2'-bromobiphenylyl-4, 2'-iodobiphenylyl-4, 4'-nitrobiphenylyl-4 or 4'-piperidinobiphenylyl-4 and Z is dialkylamino of 4–6 carbon atoms, morpholino, pyrrolidino, piperidino, homopiperidino or 3-hydroxypiperidino;
1i R is 4'-fluorobiphenylyl-4, 4'-chlorobiphenylyl-4 or 4'-nitrobiphenylyl-4, and Z is morpholino, pyrrolidino or piperidino;
1j R is 4'-fluorobiphenylyl-4, 4'-chlorobiphenylyl-4 or 4'-nitrobiphenylyl-4, $R_1$ is hydrogen, and Z is morpholino, pyrrolidino or piperidino;
1k R is 4'-fluorobiphenylyl-4, 4'-chlorobiphenylyl-4 or 4'-nitrobiphenylyl-4, $R_1$ is methyl, and Z is morpholino, pyrrolidino or piperidino;
1l R is 4'-fluorobiphenylyl-4 and Z is morpholino, pyrrolidino, piperidino, homopiperidino or 3-hydroxypiperidino;
1m R is 4'-fluorobiphenylyl-4 or 4'-chlorobiphenylyl-4 and

| | |
|---|---|
| | Z is morpholino, pyrrolidino or piperidino; |
| 1n | R is 4'-nitrobiphenylyl-4 and Z is morpholino, pyrrolidino or piperidino. |

In each of the classes of compounds defined by Formulae 1 and 1a through 1e, expressly contemplated as sub-classes thereof are those wherein Z is one only of the values given for Formula 1, viz., the sub-class wherein Z is dialkylamino, the subclass wherein Z is pyrrolidino, etc.

In a process aspect, this invention relates to a process for the production of biphenylyl ethers of Formula 1 and their physiologically acceptable acid addition salts, wherein a compound of Formula 2

$$R-O-CH_2-Y \qquad 2$$

wherein Y is

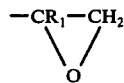

or $-CR_1(OH)-CH_2X$; X is Hal or a free or functionally modified OH-group; Hal being Cl, Br or I, and R and $R_{R1}$ have the values given for Formula I, is reacted with a compound of general Formula 3

$$H-Z \qquad 3$$

wherein Z has the values given for Formula I, and optionally thereafter a thus-obtained base of Formula 1 is converted, by treatment with an acid, into a physiologically acceptable acid addition salt or a thus-obtained acid addition salt is converted by treatment with a base into the free base of Formula 1.

These reactions occur according to methods known per se and described in detail in the literature.

In Formula 2, Y preferably is oxiranyl or 1-methyloxiranyl and X is peferably Cl or Br but can, however, also be I, OH or a functionally modified OH-group. Functionally modified OH-groups are preferably reactively esterified OH-groups, for example, alkylsulfonyloxy of preferably 1-6 carbon atoms, e.g., methanesulfonyloxy, or arylsulfonyloxy of preferably 6-10 carbon atoms, e.g., benzenesulfonyloxy, p-toluenesulfonyloxy or 1- or 2-naphthalenesulfonyloxy.

The starting compounds for the process of this invention are either known, or they can be produced according to methods known per se from the literature analogously to conventional compounds. For example, the compounds of Formula 2 are obtainable by the reaction of phenols of the formula R—OH with compounds of the formula X—CH_2—Y, e.g., epibromohydrin or epichlorohydrin. Depending on the working-up operation employed, one obtains epoxides or halohydrins of Formula 2. The epoxides have the advantage that they can be purified particularly well. The amines of Formula 3 are generally known.

The reaction of compounds of Formula 2 with compounds of Formula 3 can be accomplished in the presence or absence of an additional inert solvent at temperatures of about 0° to 200°, preferably about 50° to 120°. Suitable inert solvents are those known from the literature for such aminating reactions, for example alcohols, e.g., methanol, ethanol, isopropanol, n-butanol; ethers, e.g., diethyl ether, diisopropyl ether, tetrahydrofuran (THF), dioxane; hydrocarbons, e.g., benzene, toluene, xylene; and sulfoxides, e.g., dimethyl sulfoxide (DMSO). The amines of Formula 3 are suitably utilized at least in a molar ratio of 1:1 or in an excess (based on the compounds of Formula 2). If they are utilized in an excess, they can simultaneously serve as the reaction solvent. It is also possible to add a further base, e.g., sodium carbonate, potassium carbonate, sodium bicarbonate or potassium bicarbonate. If the starting compounds are those of Formula 2 which have such a constitution that one mole of acid is split off during the reaction (for example, the halohydrins, with hydrogen halide being split off), then it is advantageous to use either an additional base or an excess of the base of Formula 3. The required reaction times range from about 10 minutes to 7 days, depending on the starting substances employed and the reaction temperature. It is also possible to conduct the reaction under pressure, thus accelerating the reaction.

A base of Formula 1 can be converted into an acid addition salt thereof in the usual manner with the aid of an acid. Suitable for this reaction are acids yielding physiologically acceptable salts. Thus, it is possible to use inorganic or organic acids, for example, sulfuric acid, nitric acid, hydrohalic acids, e.g., hydrochloric acid or hydrobromic acid, phosphoric acids, e.g., orthophosphoric acid, as well as aliphatic, alicyclic, araliphatic, aromatic or heterocyclic mono- and polybasic carboxylic or sulfonic acids, e.g., formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicyclic acid, phenylpropionic acid, citric acid, gluconic acid, ascorbic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids. The free bases of Formula 1 can, if desired, be liberated from acid addition salts thereof by treatment with a strong base, e.g., sodium or potassium hydroxide, sodium or potassium carbonate.

The compounds of Formula 1 which contain a center of asymmetry are ordinarily obtained in the racemic form. If the compounds have two or more centers of asymmetry, they are generally obtained during the synthesis as mixtures of racemates, from which the individual racemates can be isolated, for example, by repeated recrystallization from suitable solvents, thus obtaining these racemates in the pure form.

The thus-produced racemates can be separated into their optical antipodes according to conventional methods either mechanically or chemically. Preferably, diastereomers are formed from the racemic mixture by reaction with an optically active separating agent. Suitable separating agents are, for example, optically active acids, such as D- and L-tartaric acid, dibenzoyl-D- and -L-tartaric acid, diacetyl-D and -L-tartaric acid, β-camphorsulfonic acid, D- and L-mandelic acid, D- and L-malic acid or D- and L-lactic acid.

It is also possible to obtain optically active compounds of Formula 1 according to the above-described methods directly by the use of a starting compound which is optically active.

The novel compounds of Formula 1 and the physiologically acceptable acid addition salts thereof can be used as drugs in the human or veterinary medicine in a mixture with solid, liquid and/or semiliquid excipients. Suitable carrier substances are those organic or inorganic materials suitable for parenteral, enteral or topical application and which do not react with the novel compounds, such as, for example, water, vegetable oils, polyethylene glycols, gelatin, lactose, amylose, magnesium stearate, talc, vaseline, cholesterol. Suitable for parenteral application are solutions, preferably oily or aqueous solutions, as well as suspensions, emulsions and implants. For enteral application, suitable are tablets, dragees, capsules, syrups, elixirs and suppositories, and for topical application, ointments, creams and powders. The above-mentioned compositions can optionally be sterilized or mixed with auxiliary agents, e.g., preservatives, stabilizers, wetting agents, salts for influencing the osmotic pressure, buffers, coloring, flavoring and/or aromatic substances.

The novel compounds can be administered analogously to the conventional compound clofibrate, preferably in dosages of about 20 to 2,000 mg., preferably 50 to 200 mg. per dosage unit. The daily dosage is preferably from 0.4 to 40 mg., more preferably from 1 to 4 mg. per kg. of body weight. Oral administration is preferred.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The temperatures herein are indicated in degrees Celsius.

EXAMPLE 1

A solution of 24.4 g. of 1-[4-(4-fluorophenyl)-phenoxy]-2,3-epoxy-propane and 85 g. of piperidine in 150 mg. of ethanol is refluxed for 15 hours and evaporated. The thus-obtained 1-[4-(4-fluorophenyl)-phenoxy]-3-piperidino-2-propanol is recrystallized from isopropanol, m.p. 106°–107°; hydrochloride, m.p. 196°–197°.

Analogously, using the following starting compounds:

1-[4-(4-fluorophenyl)-phenoxy]-2,3-epoxy-propane
1-[4-(4-flourophenyl)-phenoxy]-2,3-epoxy-2-methyl-propane
1-[4-(4-chlorophenyl)-phenoxy]-2,3-epoxy-propane
1-[4-(4-chlorophenyl)-phenoxy]-2,3-epoxy-2-methyl-propane
1-[4-(2-bromophenyl)-phenoxy]-2,3-epoxy-propane
1-[4-(2-bromophenyl)-phenoxy]-2,3-epoxy-2-methyl-propane
1-[4-(4-bromophenyl)-phenoxy]-2,3-epoxy-propane
1-[4-(4-bromophenyl)-phenoxy]-2,3-epoxy-2-methyl-propane
1-[4-(2-iodophenyl)-phenoxy]-2,3-epoxy-propane
1-[4-(2-iodophenyl)-phenoxy]-2,3-epoxy-2-methyl-propane
1-[4-(4-iodophenyl)-phenoxy]-2,3-epoxy-propane
1-[4-(4-iodophenyl)-phenoxy]-2,3-epoxy-2-methyl-propane
1-[4-(3-trifluoromethylphenyl)-phenoxy]-2,3-epoxy-propane
1-[4-(3-trifluoromethylphenyl)-phenoxy]-2,3-epoxy-2-methyl-propane
1-[4-(4-trifluoromethylphenyl)-phenoxy]-2,3-epoxy-propane
1-[4-(4-trifluoromethylphenyl)-phenoxy]-2,3-epoxy-2-methyl-propane
1-[4-(4-nitrophenyl)-phenoxy]-2,3-epoxy-propane
1-[4-(4-nitrophenyl)-phenoxy]-2,3-epoxy-2-methyl-propane
1-(2-phenyl-4-nitrophenoxy)-2,3-epoxy-propane
1-(2-phenyl-4-nitrophenoxy)-2,3-epoxy-2-methyl-propane
1-[4-(4-piperidinophenyl)-phenoxy]-2,3-epoxy-propane
1-[4-(4-piperidinophenyl)-phenoxy]-2,3-epoxy-2-methyl-propane the following final products are obtained with pyrrolidine, piperidine, homopiperidine, 3-hydroxypiperidine and morpholine, respectively:

1-[4-(4-fluorophenyl)-phenoxy]-3-pyrrolidino-2-propanol
1-[4-(4-fluorophenyl)-phenoxy]-3-homopiperidino-2-propanol
1-[4-(4-fluorophenyl)-phenoxy]-3-(3-hydroxypiperidino)-2-propanol
1-[4-(4-fluorophenyl)-phenoxy]-3-morpholino-2-propanol, m.p. 100°–102°
1-[4-(4-fluorophenyl)-phenoxy]-2-methyl-3-pyrrolidino-2-propanol
1-[4-(4-fluorophenyl)-phenoxy]-2-methyl-3-piperidino-2-propanol
1-[4-(4-fluorophenyl)-phenoxy]-2-methyl-3-homopiperidino-2-propanol
1-[4-(4-fluorophenyl)-phenoxy]-2-methyl-3-(3-hydroxypiperidino)-2-propanol
1-[4-(4-fluorophenyl)-phenoxy]-2-methyl-3-morpholino-2-propanol
1-[4-(4-chlorophenyl)-phenoxy]-3-pyrrolidino-2-propanol, m.p. 67°–68°/
1-[4-(4-chlorophenyl)-phenoxy]-3-piperidino-2-propanol, m.p. 116°–117°
1-[4-(4-chlorophenyl)-phenoxy]-3-homopiperidino-2-propanol
1-[4-(4-chlorophenyl)-phenoxy]-3-(3-hydroxypiperidino)-2-propanol
1-[4-(4-chlorophenyl)-phenoxy]-3-morpholino-2-propanol, m.p. 95°–97°
1-[4-(4-chlorophenyl)-phenoxy]-2-methyl-3-pyrrolidino-2-propanol
1-[4-(4-chlorophenyl)-phenoxy]-2-methyl-3-piperidino-2-propanol, m.p. 121°–122°
1-[4-(4-chlorophenyl)-phenoxy]-2-methyl-3-homopiperidino-2-propanol
1-[4-(4-chlorophenyl)-phenoxy]-2-methyl-3-(3-hydroxypiperidino)-2-propanol
1-[4-(4-chlorophenyl)-phenoxy]-2-methyl-3-morpholino-2-propanol
1-[4-(2-bromophenyl)-phenoxy]-3-pyrrolidino-2-propanol
1-[4-(2-bromophenyl)-phenoxy]-3-piperidino-2-propanol, m.p. 70°–72°
1-[4-(2-bromophenyl)-phenoxy]-3-homopiperidino-2-propanol
1-[4-(2-bromophenyl)-phenoxy]-3-(3-hydroxypiperidino)-2-propanol
1-[4-(2-bromophenyl)-phenoxy]-3-morpholino-2-propanol
1-[4-(2-bromophenyl)-phenoxy]-2-methyl-3-pyrrolidino-2-propanol
1-[4-(2-bromophenyl)-phenoxy]-2-methyl-3-piperidino-2-propanol
1-[4-(2-bromophenyl)-phenoxy]-2-methyl-3-homopiperidino-2-propanol 1-[4-(2-bromophenyl)-phenoxy]-2-methyl-3-(3-hydroxypiperidino)-2-propanol
1-[4-(2-bromophenyl)-phenoxy]-2-methyl-3-morpholino-2-propanol
1-[4-(4-bromophenyl)-phenoxy]-3-pyrrolidino-2-propanol
1-[4-(4-bromophenyl)-phenoxy]-3-piperidino-2-propanol, m.p. 121°–122°
1-[4-(4-bromophenyl)-phenoxy]-3-homopiperidino-2-propanol
1-[4-(4-bromophenyl)-phenoxy]-3-(3-hydroxypiperidino)-2-propanol
1-[4-(4-bromophenyl)-phenoxy]-3-morpholino-2-propanol
1-[4-(4-bromophenyl)-phenoxy]-2-methyl-3-pyrrolidino-2-propanol
1-[4-(4-bromophenyl)-phenoxy]-2-methyl-3-piperidino-2-propanol
1-[4-(4-bromophenyl)-phenoxy]-2-methyl-3-homopiperidino-2-propanol
1-[4-(4-bromophenyl)-phenoxy]-2-methyl-3-(3-hydroxypiperidino)-2-propanol
1-[4-(4-bromophenyl)-phenoxy]-2-methyl-3-morpholino-2-propanol
1-[4-(2-iodophenyl)-phenoxy]-3-pyrrolidino-2-propanol
1-(4-(2-iodophenyl)-phenoxy]-3-piperidino-2-propanol, m.p. 72°–76°
1-[4-(2-iodophenyl)-phenoxy]-3-homopiperidino-2-propanol
1-[4-(2-iodophenyl)-phenoxy]-3-(3-hydroxypiperidino)-2-propanol
1-[4-(2-iodophenyl)-phenoxy]-3-morpholino-2-propanol
1-[4-(2-iodophenyl)-phenoxy]-2-methyl-3-pyrrolidino-2-propanol
1-[4-(2-iodophenyl)-phenoxy]-2-methyl3-piperidino-2-propanol
1-[4-(2-iodophenyl)-phenoxy]-2-methyl-3-homopiperidino-2-propanol
1-[4-(2-iodophenyl)-phenoxy]-2-methyl-3-(3-hydroxypiperidino)-2-propanol
1-[4-(2-iodophenyl)-phenoxy]-2-methyl-3-morpholino-2-propanol
1-[4-(4-iodophenyl)-phenoxy]-3-pyrrolidino-2-propanol
1-[4-(4-iodophenyl)-phenoxy]-3-piperidino-2-propanol, m.p. 123°–124°
1-[4-(4-iodophenyl)-phenoxy]-3-homopiperidino-2-propanol
1-[4-(4-iodophenyl)-phenoxy]-3-(3-hydroxypiperidino)-2-propanol
1-[4-(4-iodophenyl)-phenoxy]-3-morpholino-2-propanol
1-[4-(4-iodophenyl)-phenoxy]-2-methyl-3-pyrrolidino-2-propanol
1-[4-(4-iodophenyl)-phenoxy]-2-methyl-3-piperidino-2-propanol
1-[4-(4-iodophenyl)-phenoxy]-2-methyl-3-homopiperidino-2-propanol
1-[4-(4-iodophenyl)-phenoxy]-2-methyl-3-(3-hydroxypiperidino)-2-propanol
1-[4-(4-iodophenyl)-phenoxy]-2-methyl-3-morpholino-2-propanol
1-[4-(3-trifluoromethylphenyl)-phenoxy]-3-pyrrolidino-2-propanol
1-[4-(3-triflouromethylphenyl)-phenoxy]-3-piperidino-2-propanol
1-[4-(3-trifluoromethylphenyl)-phenoxy]-3-homopiperidino-2-propanol
1-[4-(3-trifluoromethylphenyl)-phenoxy]-3-(3-hydroxypiperidino)-2-propanol
1-[4-(3-trifluoromethylphenyl)-phenoxy]-3-morpholino-2-propanol
1-[4-(3-trifluoromethylphenyl)-phenoxy]-2-methyl-3-pyrrolidino-2-propanol
1-[4-(3-trifluoromethylphenyl)-phenoxy]-2-methyl-3-piperidino-2-propanol
1-[4-(3-trifluoromethylphenyl)-phenoxy]-2-methyl-3-homopiperidino-2-propanol
1-[4-(3-trifluoromethylphenyl)-phenoxy]-2-methyl-3-(3-hydroxypiperidino)-2-propanol
1-[4-(3-trifluoromethylphenyl)-phenoxy]-2-methyl-3-morpholino-2-propanol
1-[4-(4-trifluoromethylphenyl)-phenoxy]-3-pyrrolidino-2-propanol
1-[4-(4-trifluoromethylphenyl)-phenoxy]-3-piperidino-2-propanol
1-[4-(4-trifluoromethylphenyl)-phenoxy]-3-homopiperidino-2-propanol
1-[4-(4-trifluoromethylphenyl)-phenoxy]-3-(3-hydroxypiperidino)-2-propanol
1-[4-(4-trifluoromethylphenyl)-phenoxy]-3-morpholino-2-propanol
1-[4-(4-trifluoromethylphenyl)-phenoxy]-2-methyl-3-pyrrolidino-2-propanol
1-( 4-(4-trifluoromethylphenyl)-phenoxy]-2-methyl-3-piperidino-2-propanol
1-( 4-(4-trifluoromethylphenyl)-phenoxy]-2-methyl-3-homopiperidino-2-propanol
1-[4-(4-trifluoromethylphenyl)-phenoxy]-2-methyl-3-(3-hydroxy-piperidino)-2-propanol
1-[4-(4-trifluoromethylphenyl)-phenoxy]-2-methyl-3-morpholino-2-propanol
1-[4-(4-nitrophenyl)-phenoxy]-3-pyrrolidino-2-propanol, m.p. 100°–102°; hydrochloride, m.p. 184°
1-[4-(4-nitrophenyl)-phenoxy]-3-piperidino-2-propanol, m.p. 115°–116°
1-[4-(4-nitrophenyl)-phenoxy]-3-homopiperidino-2-propanol
1-[4-(4-nitrophenyl)-phenoxy]-3-(3-hydroxypiperidino)-2-propanol
1-[4-(4-nitrophenyl)-phenoxy]-3-morpholino-2-propanol, m.p. 152°; hydrochloride, m.p. 213°
1-[4-(4-nitrophenyl)-phenoxy]-2-methyl-3-pyrrolidino-2-propanol
1-[4-(4-nitrophenyl)-phenoxy]-2-methyl-3-piperidino-2-propanol
1-[4-(4-nitrophenyl)-phenoxy]-2-methyl-3-homopiperidino-2-propanol
1-[4-(4-nitrophenyl)-phenoxy]-2-methyl-3-(3-hydroxypiperidino)-2-propanol
1-[4-(4-nitrophenyl)-phenoxy]-2-methyl-3-morpholino-2-propanol
1-(2-phenyl-4-nitrophenoxy)-3-pyrrolidino-2-propanol, m.p. 82°–85°
1-(2-phenyl-4-nitrophenoxy)-3-piperidino-2-propanol, m.p. 94°–95°
1-(2-phenyl-4-nitrophenoxy)-3-homopiperidino-2-propanol
1-(2-phenyl-4-nitrophenoxy)-3-(3-hydroxypiperidino)-2-propanol
1-(2-phenyl-4-nitrophenoxy)-3-morpholino-2-propanol
1-(2-phenyl-4-nitrophenoxy)-2-methyl-3-pyrrolidino-2-propanol 1-(2-phenyl-4-nitrophenoxy)-2-methyl-3-piperidino-2-propanol
1-(2-phenyl-4-nitrophenoxy)-2-methyl-3-homopiperidino-2-propanol
1-(2-phenyl-4-nitrophenoxy)-2-methyl-3-(3-hydroxypiperidino)-2-propanol
1-(2-phenyl-4-nitrophenoxy)-2-methyl-3-morpholino-2-propanol
1-[4-(4-piperidinophenyl)-phenoxy]-3-pyrrolidino-2-propanol, m.p. 120°–123°
1-[4-(4-piperidinophenyl)-phenoxy]-3-piperidino-2-propanol, m.p. 123°–125°
1-[4-(4-piperidinophenyl)-phenoxy]-3-homopiperidino-2-propanol
1-[4-(4-piperidinophenyl)-phenoxy]-3-(3-hydroxypiperidino)-2-propanol
1-[4-(4-piperidinophenyl)-phenoxy]-3-morpholino-2-propanol
1-[4-(4-piperidinophenyl)-phenoxy]-2-methyl-3-pyrrolidino-2-propanol, m.p. 116°–121°
1-[4-(4-piperidinophenyl)-phenoxy]-2-methyl-3-piperidino-2-propanol, m.p. 137°–138°
1-[4-(4-piperidinophenyl)-phenoxy]-2-methyl-3-homopiperidino-2-propanol, m.p. 124°–126°
1-[4-(4-piperidinophenyl)-phenoxy]-2-methyl-3-(3-hydroxypiperidino)-2-propanol, m.p. 148°–149°
1-[4-(4-piperidinophenyl)-phenoxy]-2-methyl-3-morpholino-2-propanol.

EXAMPLE 2

A mixture of 3.09 g. of 1-[4-(4-piperidinophenyl)-phenoxy]-2,3-epoxypropane (obtainable from 4'-piperidino-4-hydroxydiphenyl and epichlorohydrin), 15 ml. of DMSO, and 25 ml. of piperidine is heated overnight to 100°. The mixture is then poured on ice water; the thus-precipitated 1-[4-(4-piperidinophenyl)-phenoxy]-3-piperidino-2-propanol is filtered and washed with water; m.p. 123°–125° (from isopropanol).

EXAMPLE 3

A mixture of 2.71 g. of 1-[4-(4-nitrophenyl)-phenoxy]-2,3-epoxypropane (obtainable from 4'-nitro-4-hydroxydiphenyl and epichlorohydrin) and 20 ml. of piperidine is heated overnight to 100°. The mixture is then evaporated, and the thus-obtained 1-[4-(4-nitrophenyl)-phenoxy]-3-piperidino-2-propanol is recrystallized from isopropanol; m.p. 115°–116°.

EXAMPLE 4

Analogously to Example 1, using the following starting compounds:
1-[4-(2-fluorophenyl)-phenoxy]-2,3-epoxy-propane
1-[4-(3-fluorophenyl)-phenoxy]-2,3-epoxy propane
1-[4-(2-chlorophenyl)-phenoxy]-2,3-epoxy-propane
1-[4-(3-chlorophenyl)-phenoxy]-2,3-epoxy-propane
1-[3-(4-fluorophenyl)-phenoxy]-2,3-epoxy-propane
1-[3-(4-chlorophenyl)-phenoxy]-2,3-epoxy-propane
1-(2-phenyl-4-chlorophenoxy)-2,3-epoxy-propane
1-[4-(3-chloro-4-fluorophenyl)-phenoxy]-2,3-epoxy-propane
1-[2-bromo-4-(4-fluorophenyl)-phenoxy]-2,3-epoxy-propane
1-[2-bromo-4-(4-chlorophenyl)-phenoxy]-2,3-epoxy-propane
1-[4-(2,4-difluorophenyl)-phenoxy]-2,3-epoxy-propane The following final products are obtained with piperidine:

1-[4-(2-fluorophenyl)-phenoxy]-3-piperidino-2-propanol
1-[4-(3-fluorophenyl)-phenoxy]-3-piperidino-2-propanol
1-[4-(2-chlorophenyl)-phenoxy]-3-piperidino-2-propanol
1-[4-(3-chlorophenyl)-phenoxy]-3-piperidino-2-propanol
1-[3-(4-fluorophenyl)-phenoxy]-3-piperidino-2-propanol
1-[3-(4-chlorophenyl)-phenoxy]-3-piperidino-2-propanol
1-(2-phenyl-4-chlorophenoxy)-3-piperidino-2-propanol
1-[4-(3-chloro-4-fluorophenyl)-phenoxy]-3-piperidino-2-propanol
1-[2-bromo-4-(4-fluorophenyl)-phenoxy]-3-piperidino-2-propanol
1-[2-bromo-4-(4-chlorophenyl)-phenoxy]-3-piperidino-2-propanol
1-[4-(2,4-difluorophenyl)-phenoxy]-3-piperidino-2-propanol.

EXAMPLE 5

In the same manner as Example 1, by the reaction of 1-(biphenylyl-4-oxy)-2,3-epoxy-propane with 3-hydroxypiperidino, there is obtained 1-(biphenylyl-4-oxy)-3-(3-hydroxy-piperidino)-2-propanol, m.p. 109°–111°.

In an analogous manner, the following compounds are produced employing the corresponding epoxide and amine:

1-(biphenylyl-4-oxy)-3-homopiperidino-2-propanol, m.p. 68°–69°
1-(biphenylyl-4-oxy)-3-(3-hydroxy-pyrrolidino)-2-propanol
1-(biphenylyl-4-oxy)-3-(4-hydroxy-piperidino)-2-propanol, m.p. 89°–90°
1-(biphenylyl-4-oxy)-3-(3-hydroxy-homopiperidino)-2-propanol
1-(biphenylyl-4-oxy)-3-(4-hydroxy-homopiperidino)-2-propanol
1-(biphenylyl-4-oxy)-2-methyl-3-pyrrolidino-2-propanol, m.p. 74°–75°
1-(biphenylyl-4-oxy)-2-methyl-3-piperidino-2-propanol, m.p. 94°–95°
1-(biphenylyl-4-oxy)-2-methyl-3-homopiperidino-2-propanol
1-(biphenylyl-4-oxy)-2-methyl-3-(3-hydroxypiperidino)-2-propanol
1-(biphenylyl-4-oxy)-2-methyl-3-morpholino-2-propanol, m.p. 82°–84°
1-(biphenylyl-2-oxy)-3-homopiperidino-2-propanol
1-(biphenylyl-2-oxy)-3-(3-hydroxy-piperidino)-2-propanol
1-(biphenylyl-2-oxy)-2-methyl-3-pyrrolidino-2-propanol
1-(biphenylyl-2-oxy)-2-methyl-3-piperidino-2-propanol, $n_D^{20}$ 1,5618
1-(biphenylyl-2-oxy)-2-methyl-3-homopiperidino-2-propanol
1-(biphenylyl-2-oxy)-2-methyl-3-(3-hydroxypiperidino)-2-propanol
1-(biphenylyl-2-oxy)-2-methyl-3-morpholino-2-propanol
1-(biphenylyl-3-oxy)-3-homopiperidino-2-propanol
1-(biphenylyl-3-oxy)-3-(3-hydroxypiperidino)-2-propanol 1-(biphenylyl-3-oxy)-2-methyl-3-pyrrolidino-2-propanol
1-(biphenylyl-3-oxy)-2-methyl-3-piperidino-2-propanol
1-(biphenylyl-3-oxy)-2-methyl-3-homopiperidino-2-propanol
1-(biphenylyl-3-oxy)-2-methyl-3-(3-hydroxypiperidino)-2-propanol
1-(biphenylyl-3-oxy)-2-methyl-3-morpholino-2-propanol.

EXAMPLE 6

A mixture of 28.05 g. of 1-[4-(4-fluorophenyl)-phenoxy]-3-chloro-2-propanol and 85 g. of piperidine is heated for 10 hours to 100°. The mixture is then evaporated and the thus-obtained 1-[4-(4-fluorophenyl)-phenoxy]-3-piperidino-2-propanol is recrystallized from isopropanol, m.p. 106°-107°.

The following examples relate to pharmaceutical preparations containing biphenylyl ethers of the general Formula 1.

EXAMPLE A

Tablets:

A mixture consisting of 100 kg. of 1-[4-(4-fluorophenyl)-phenoxy]-3-piperidino-2-propanol, 500 kg. of lactose, 160 kg. of corn starch, 20 kg. of cellulose powder, and 20 kg. of magnesium stearate is compressed into tablets in the usual manner, so that each tablet contains 100 mg. of active agent.

EXAMPLE B

Dragees:

Analogously to Example A, tablets are compressed and subsequently coated by the usual method with a layer consisting of sugar, corn starch, talc, and tragacanth.

EXAMPLE C

Capsules:

A mixture consisting of 150 kg. of 1-[4-(4-fluorophenyl)-phenoxy]-3-piperidino-2-propanol, 1.5 kg. of finely dispersed silicic acid, 7.5 kg. of talc, and 0.8 kg. of Mg stearate is filled into hard gelatin capsules in the usual manner, so that each capsule contains 150 mg. of the active agent.

Analogously, tablets, dragees, and capsules can be obtained which contain one or more of the other effective agents of Formula 1 and/or the physiologically acceptable acid addition salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A biphenylyl ether of the formula R—O—CH$_2$—CH(OH)—CH$_2$Z wherein Z is piperidino and R is biphenylyl-4 substituted in the 4'-position by F, Cl, Br, I, CF$_3$, NO$_2$ or piperidino; or a physiologically acceptable acid addition salt thereof.

2. A compound of claim 1, 1-[4-(4-trifluoromethylphenyl)-phenoxy]-3-piperidino-2-propanol or a physiologically acceptable acid addition salt thereof.

3. A compound of claim 1, 1-[4-(4-fluorophenyl)-phenoxy]-3-piperidino-2-propanol or a physiologically acceptable acid addition salt thereof.

4. A compound of claim 1, 1-[4-(4-chlorophenyl)-phenoxy]-3-piperidino-2-propanol or a physiologically acceptable acid addition salt thereof.

5. A compound of claim 1, 1-[4-(4-bromophenyl)-phenoxy]-3-piperidino-2-propanol or a physiologically acceptable acid addition salt thereof.

6. A compound of claim 1, 1-[4-(4-iodophenyl)-phenoxy]-3-piperidino-2-propanol or a physiologically acceptable acid addition salt thereof.

7. A compound of claim 1, 1-[4-(4-nitrophenyl)-phenoxy]-3-piperidino-2-propanol or a physiologically acceptable acid addition salt thereof.

8. A compound of claim 1, 1-[4-(4-piperidinophenyl)-phenoxy]-3-piperidino-2-propanol or a physiologically acceptable acid addition salt thereof.

9. A biphenylyl ether of the formula R—O—CH$_2$—CCH$_3$(OH)—CH$_2$Z wherein Z is morpholino, pyrrolidino, piperidino or homopiperidino, hydroxypiperidino or hydroxyhomopiperidino, and R is biphenylyl-4 substituted in the 4'-position by F, Cl, Br, I, CF$_3$, NO$_2$ or piperidino; or a physiologically acceptable acid addition salt thereof.

10. A compound of claim 9 wherein Z is pyrrolidino.

11. A compound of claim 9 wherein Z is piperidino.

12. A compound of claim 9 wherein Z is morpholino.

13. A compound of claim 9, 1-[4-(4-chlorophenyl)-phenoxy]-2-methyl-3-piperidino-2-propanol or a physiologically acceptable acid addition salt thereof.

14. A compound of claim 9, 1-[4-(4-piperidinophenyl)-phenoxy]-2-methyl-3-pyrrolidino-2-propanol or a physiologically acceptable acid addition salt thereof.

15. A compound of claim 9, 1-[4-(4-piperidinophenyl)-phenoxy]-2-methyl-3-piperidino-2-propanol or a physiologically acceptable acid addition salt thereof.

16. A compound of claim 9, 1-[4-(4-piperidinophenyl)-phenoxy]-2-methyl-3-homopiperidino-2-propanol or a physiologically acceptable acid addition salt thereof.

17. A compound of claim 9, 1-[4-(4-piperidinophenyl)-phenoxy]-2-methyl-3-(3-hydroxypiperidino)-2-propanol or a physiologically acceptable acid addition salt thereof.

18. 1-(2-phenyl-4-nitrophenoxy)-3-piperidino-2-propanol or a physiologically acceptable acid addition salt thereof.

19. 1-[4-(4-piperidinophenyl)-phenoxy]-3-pyrrolidino-2-propanol or a physiologically acceptable acid addition salt thereof.

20. A pharmaceutical composition comprising at least a cholesterol blood serum lowering amount per unit dosage of one compound of claim 1 or a physiologically acceptable acid addition salt thereof in admixture with a pharmaceutically acceptable carrier.

21. A method of lowering abnormally high blood serum cholesterol levels which comprises administering systemically to the affected patient an amount of a compound of claim 1 effective to lower the abnormally high cholesterol level.

* * * * *